United States Patent
DeLuca et al.

(10) Patent No.: US 9,947,212 B2
(45) Date of Patent: *Apr. 17, 2018

(54) WEARABLE DEVICE CONFIGURATION INTERACTION

(71) Applicant: INTERNATIONAL BUSINESS MACHINES CORPORATION, Armonk, NY (US)

(72) Inventors: Lisa Seacat DeLuca, Baltimore, MD (US); Clifford A. Pickover, Yorktown Heights, NY (US); Dana L. Price, Surf City, NC (US); Aaron J. Quirk, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/713,818

(22) Filed: Sep. 25, 2017

(65) Prior Publication Data

US 2018/0040231 A1 Feb. 8, 2018

Related U.S. Application Data

(63) Continuation of application No. 15/227,114, filed on Aug. 3, 2016.

(51) Int. Cl.
| | | |
|---|---|---|
| G08B 25/01 | (2006.01) | |
| G08B 25/00 | (2006.01) | |
| A61B 5/00 | (2006.01) | |
| A61B 5/024 | (2006.01) | |

(52) U.S. Cl.
CPC ........ G08B 25/016 (2013.01); A61B 5/02438 (2013.01); A61B 5/681 (2013.01); G08B 25/008 (2013.01)

(58) Field of Classification Search
CPC .... G08B 25/016; G08B 25/008; A61B 5/681; A61B 5/02438
See application file for complete search history.

(56) References Cited

U.S. PATENT DOCUMENTS

| | | |
|---|---|---|
| 9,041,675 B2 | 5/2015 | Cho et al. |
| 9,086,687 B2 | 7/2015 | Park et al. |

(Continued)

OTHER PUBLICATIONS

Bump Blog; retrieved from the Internet on Mar. 144, 2016; URL: http://blog.bu.mp/; 7 pages.

(Continued)

*Primary Examiner* — Leon Flores
(74) *Attorney, Agent, or Firm* — Schmeiser, Olsen & Watts; John R. Pivnichny

(57) ABSTRACT

A method and system for interacting with a wearable device is provided. The method includes detecting, by a first wearable device of a first user, a body attachment band of a second wearable device of a second user physically interlinked with a body attachment band of the first wearable device. In response, operational attributes of the first wearable device are activated and a specified configuration between the body attachment band of the first wearable device and the body attachment band of the second wearable device is detected. Specified actions associated with the operational attributes are determined and a specified action is executed with respect to a first operational attribute. The specified action is executed with respect to the first wearable device and the second wearable device.

20 Claims, 5 Drawing Sheets

(56) References Cited

U.S. PATENT DOCUMENTS

| | | |
|---|---|---|
| 2015/0015502 A1 | 1/2015 | Al-Nasser |
| 2015/0111558 A1 | 4/2015 | Yang |
| 2015/0149116 A1 | 5/2015 | Cho et al. |
| 2015/0153854 A1 | 6/2015 | Stewart et al. |
| 2015/0177939 A1 | 6/2015 | Anderson et al. |
| 2015/0186609 A1 | 7/2015 | Utter, II |
| 2015/0301608 A1 | 10/2015 | Nagaraju et al. |
| 2015/0334189 A1 | 11/2015 | Hwang |
| 2015/0338236 A1 | 11/2015 | Hoffman et al. |
| 2015/0338926 A1 | 11/2015 | Park et al. |
| 2015/0370326 A1 | 12/2015 | Chapeskie et al. |

OTHER PUBLICATIONS

Houben, Steven et al.; WatchConnect: A Toolkit for prototyping Smartwatch-Centric Cross-Device Applications; CHI 2015 Smartwatch Interaction; Apr. 18-23, 2015; pp. 1247-1256.

Intelligence; The Wearables Report: Growth trends, consumer attitudes, and why smartwatches will dominate; Business Insider; May 21, 2015; 4 pages.

Leo, Pietro; AoT Top 10 Theme: Wearable Computing; May 6, 2015; retrieved from the Internet on Mar. 14, 2016 URL: https://learning3.atlanta.ibm.com/hr/global/events/ems.nsf/pp./tle-sess . . . ; 1 page.

Painter, Lewis; How to use Digital Touch on Apple Watch: Guide to sending a Digital Touch on Apple's smartwatch; Macworld; Apr. 28, 2015; 9 pages.

Stanimirovic, Darko et al.; [Poster] Smartwatch-Aided Handheld Augmented Reality; IEEE International Symposium on Mixed and Augmented Reality 2014 Science and Technology Proceedings; Sep. 10-12, 2014; pp. 307-308.

Vega, Armando et al.; Smartwatch as a Remote Server Monitoring Device: Implementation and Interaction Design; MIPRO 2015; May 25-29, 2015; pp. 566-571.

Friedman, Mark J.; List of IBM Patents or Patent Applications Treated as Related; Sep. 25, 2017; 1 page.

WEARABLE DEVICE CONFIGURATION INTERACTION

This application is a continuation application claiming priority to Ser. No. 15/227,114 filed Aug. 3, 2016.

FIELD

The present invention relates generally to a method for sensing interacting arrangements between wearable devices and in particular to a method and associated system for improving communications technology by generating wearable device actions based on an interlinking arrangement between wearable devices.

BACKGROUND

Smart watches for communicating information to a user are well known. A large number of solutions currently exist with respect establishing communications between smart watches. However, establishing a trust agreement between smart watches may include a complicated process that may be time consuming and require a large amount of resources. Current solutions for establishing trusted communications between smart watches typically include an inaccurate process with little flexibility.

Therefore, the aforementioned solutions may be associated with inaccurate results. As a result, the current solutions do not comprise an effective means for accurately establishing trusted communications between smart watches.

Accordingly, there exists a need in the art to enable accurate and trusted communications between smart watches

SUMMARY

A first aspect of the invention provides a wearable device interaction method comprising: detecting, by a processor of a first wearable device of a first user, a body attachment band of a second wearable device of a second user physically interlinked with a body attachment band of the first wearable device, wherein the body attachment band of the first wearable device comprises an apparatus for attaching the first wearable device to a forearm of the first user, and wherein the body attachment band of the second wearable device comprises an apparatus for attaching the second wearable device to a forearm of the second user; activating, by the processor in response to the detecting, operational attributes of the first wearable device; detecting, by the processor, a specified configuration between the body attachment band of the first wearable device and the body attachment band of the second wearable device; determining, by the processor, specified actions associated with the operational attributes; and executing, by the processor based on the specified configuration, a first specified action of the specified actions with respect to a first operational attribute of the operational attributes, the first specified action being executed with respect to the first wearable device and the second wearable device.

A second aspect of the invention provides a computer program product, comprising a computer readable hardware storage device storing a computer readable program code, the computer readable program code comprising an algorithm that when executed by a processor of a first wearable device of a first user implements a wearable device interaction method, the method comprising: detecting, by the processor, a body attachment band of a second wearable device of a second user physically interlinked with a body attachment band of the first wearable device, wherein the body attachment band of the first wearable device comprises an apparatus for attaching the first wearable device to a forearm of the first user, and wherein the body attachment band of the second wearable device comprises an apparatus for attaching the second wearable device to a forearm of the second user; activating, by the processor in response to the detecting, operational attributes of the first wearable device; detecting, by the processor, a specified configuration between the body attachment band of the first wearable device and the body attachment band of the second wearable device; determining, by the processor, specified actions associated with the operational attributes; and executing, by the processor based on the specified configuration, a first specified action of the specified actions with respect to a first operational attribute of the operational attributes, the first specified action being executed with respect to the first wearable device and the second wearable device.

A third aspect of the invention provides a first wearable device of a first user comprising a processor coupled to a computer-readable memory device, the memory device comprising instructions that when executed by the processor implements a wearable device interaction method, the method comprising: detecting, by the processor, a body attachment band of a second wearable device of a second user physically interlinked with a body attachment band of the first wearable device, wherein the body attachment band of the first wearable device comprises an apparatus for attaching the first wearable device to a forearm of the first user, and wherein the body attachment band of the second wearable device comprises an apparatus for attaching the second wearable device to a forearm of the second user; activating, by the processor in response to the detecting, operational attributes of the first wearable device; detecting, by the processor, a specified configuration between the body attachment band of the first wearable device and the body attachment band of the second wearable device; determining, by the processor, specified actions associated with the operational attributes; and executing, by the processor based on the specified configuration, a first specified action of the specified actions with respect to a first operational attribute of the operational attributes, the first specified action being executed with respect to the first wearable device and the second wearable device.

The present invention advantageously provides a simple method and associated system capable of communicating information to a user.

DETAILED DESCRIPTION

Figure 1:
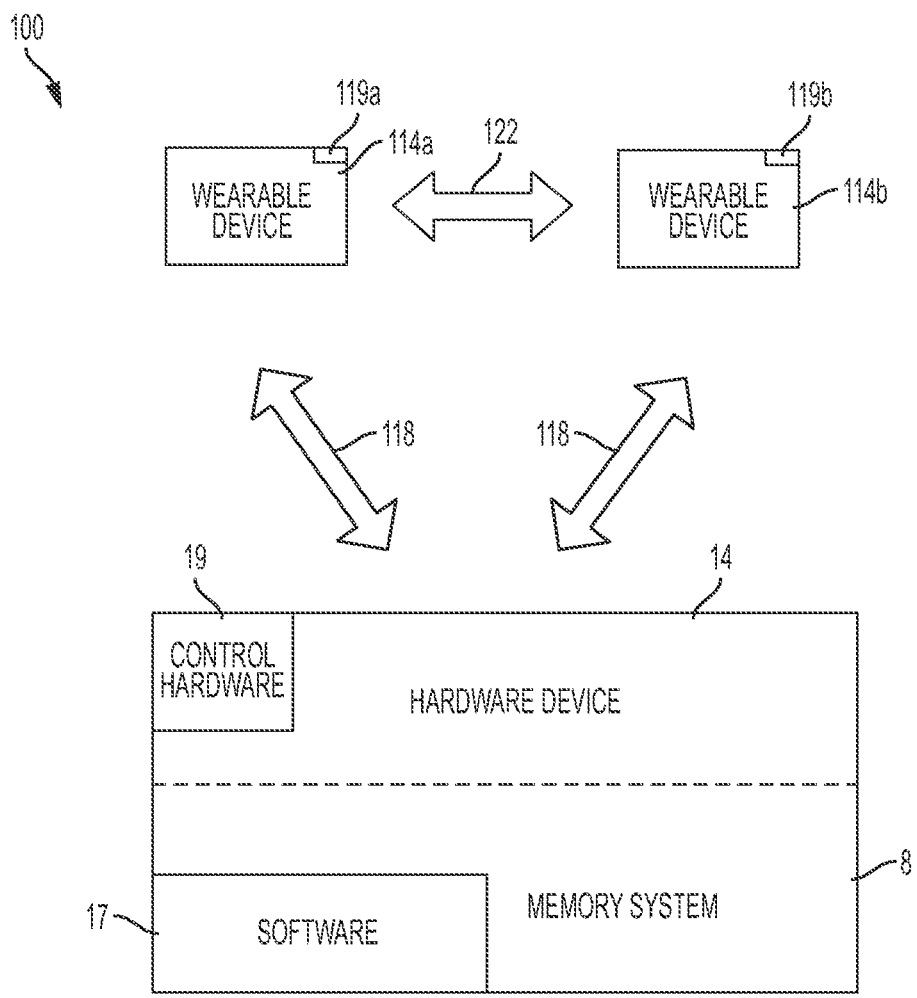
FIG. 1 illustrates a system for executing wearable device actions based on a detected configuration between multiple wearable devices, in accordance with embodiments of the present invention.
Figure 2:
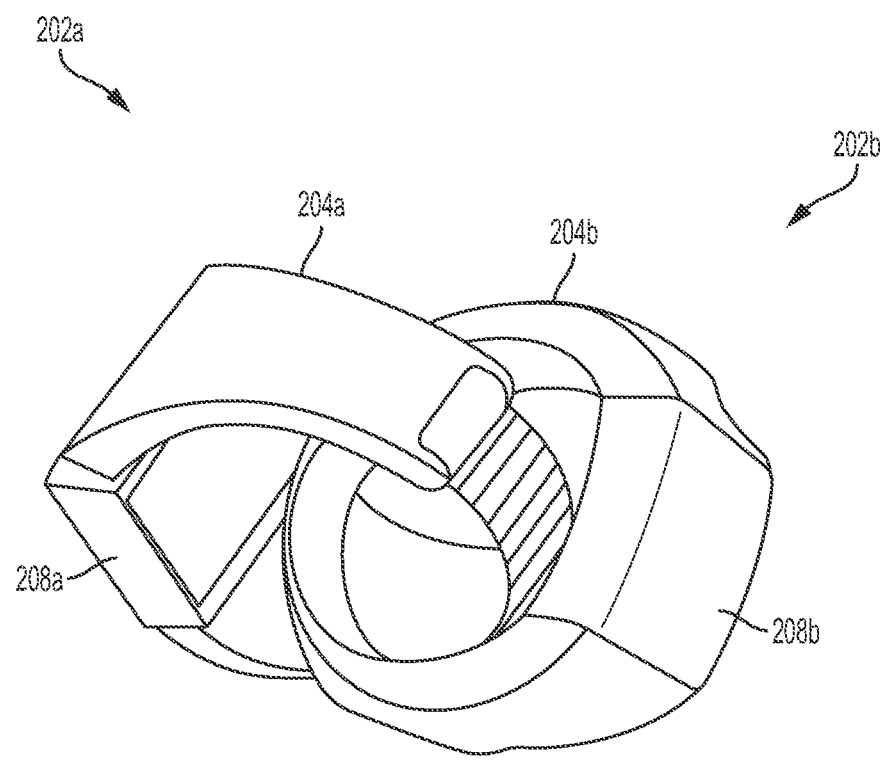
FIG. 2 illustrates an interlinking implementation scenario enabled by the system of FIG. 1, in accordance with embodiments of the present invention.
Figure 3:
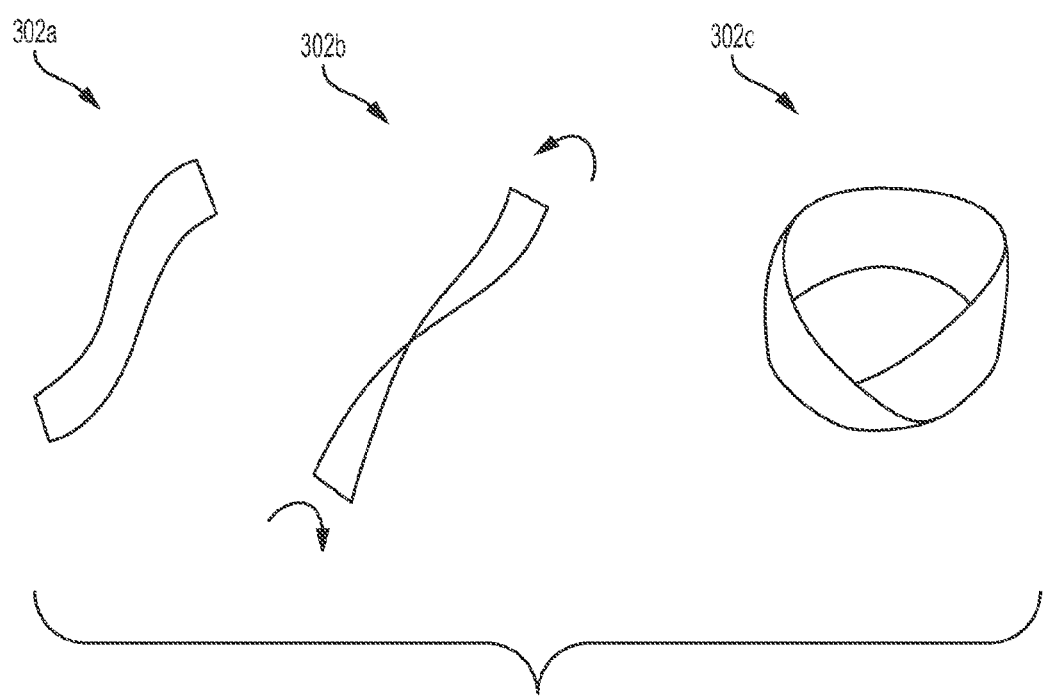
FIG. 3 illustrates an attachment band implementation scenario enabled by the system of FIG. 1, in accordance with embodiments of the present invention.

FIG. 1 illustrates a system 100 for executing wearable device actions based on a detected configuration between multiple wearable devices, in accordance with embodiments of the present invention. System 100 enables an improvement to a process for executing communication/integration actions between wearable (hardware) devices 114a ... 114b based on a detected configuration (or relationship) between any portion of wearable devices 114a ... 114b. For example, detected configurations may include, inter alia, an attachment band (e.g., a band securing the wearable device to a user's wrist such as a watch band) for a display portion (e.g., a smart watch portion) of wearable device 114a interlinking with an attachment band for wearable device 114b (similar to two links in a chain as illustrated in FIG. 2, infra), a back portion of wearable device 114a in physical contact with a back portion of wearable device 114b, specified twist configurations of attachment bands for wearable devices 114a and/or 114b (as illustrated in FIG. 3, infra), etc. The aforementioned detected configurations may be enabled to control a functionality between wearable device 114a and wearable device 114n (e.g., communications, an exchange of information, a trust agreement, etc.). Alternatively or additionally, wearable device 114a and wearable device 114b may comprise an interface including switches (mechanical or virtual) for controlling a functionality of wearable device 114a and/or wearable device 114b.

System 100 of FIG. 1 includes wearable devices 114a and 114b communicatively connected to each other via a wireless network 122 or wireless pairing such that actions are executed by wearable device 114a and/or 114b based on a detected configuration between wearable devices 114a and 114b. Additionally and alternatively, system 100 of FIG. 1 may include wearable devices 114a and 114b communicatively connected to an optional hardware device 14 (alternatively executing actions based on a detected configuration between wearable devices 114a and 114b) via a wireless network 118. Wearable devices 114a and 114b may comprise any type of mobile hardware wearable communication device including, inter alia, a smart watch (comprising a watch and a band), a wearable mobile phone, a wearable PDA, a specialized wearable hardware device, etc. Hardware device 14 may comprise any type of communication device including, inter alia, a mobile phone, a PDA, a specialized hardware device, a server, etc. Wearable devices 114a and 114b (i.e., control hardware/action taking component 119a and 119b internal to wearable devices 114a and 114b) and hardware device 14 each may comprise an embedded computer. An embedded computer is defined herein as a remotely portable dedicated computer comprising a combination of computer hardware and software (fixed in capability or programmable) specifically designed for executing a specialized function. Programmable embedded computers may comprise specialized programming interfaces. Additionally, wearable devices 114a and 114b (i.e., control hardware/action taking component 119a and 119b internal to wearable devices 114a and 114b) and hardware device 14 may each comprise a specialized hardware device comprising specialized (non-generic) hardware and circuitry (i.e., specialized discrete non-generic analog, digital, and logic based circuitry) for executing a process described with respect to FIGS. 1-4. The specialized discrete non-generic analog, digital, and logic based circuitry may include proprietary specially designed components (e.g., a specialized integrated circuit designed for only implementing an automated process for executing wearable device actions based on a detected configuration between multiple wearable devices 114a and 114b). Hardware device 14 includes a memory system 8, software 17, and control hardware 19 (i.e., all sensors and associated control hardware for enabling software 17 to execute for executing wearable device actions based on a detected configuration between multiple wearable devices). The memory system 8 may include a single memory system. Alternatively, the memory system may include a plurality of memory systems. Control hardware 19 may include sensors for detecting and communicating with wearable devices 114a and 114b. Additionally, wearable devices 114a and 114b may include sensors for detecting configuration (or relationship) between wearable devices 114a ... 114b such as an attachment band interlinking configuration, back portions of wearable device 114a and 114b in physical contact with each other, specified twist configurations of attachment bands for wearable devices 114a and/or 114b, etc. Sensors may include, inter alia, GPS sensors, video recording devices, optical sensors, weight sensors, RFID sensors, Bluetooth sensors, NFC sensors, an accelerometer, a humidity sensor, a pressure sensor, a proximity sensor, a temperature sensor, a heart rate monitor, a motion sensor, etc.

Control hardware/action taking components 119a and 119b execute actions based on detected configurations of wearable devices 114a and/or 114b with respect to each other (e.g., attachment bands being interlinked). Actions may include, inter alia, a security change (e.g. associated with wearable devices 114a and/or 114b), enabling communication between wearable devices 114a and/or 114b, confirmation processes with respect to wearable devices 114a and/or 114b, enabling an alarm, etc. An enabled alarm may be disabled by, inter alia, applying pressure to any portion of wearable devices 114a and/or 114b (e.g., to a band or a communication portion). Detected configurations of wearable devices 114a and/or 114b may be used to validate an affirmation or trusted connection between individuals exchanging information via wearable devices 114a and 114b. Each of wearable devices 114a and/or 114b may comprise control functionality for adjusting security functions associated with wearable device interfaces (e.g., a computing portion such as a smart watch portion). Additionally, various icons may be located on within a graphical user interface (GUI) of wearable devices 114a and 114b for enabling users to transmit and receive messages and/or perform additional inter-wearable device functions. Wearable devices 114a and/or 114b may additionally include electronic circuitry comprising a transceiver for receiving and transmitting messages. Attachment bands for wearable device 114a and/or 114b may optionally include electrically conductive fibers electrically connected to a wearable device interface (e.g., watch portion) thereby creating an electronic circuit between the attachment band and the wearable device interface. Additionally, a power source may be integrated with the electrically conductive fibers fabricating the attachment band. The attachment band may include a rotatable flexible GUI screen such as, inter alia, a bendable flexible display screen and associated band, a flexible display screen elastic support frame, a flexible display screen rotation structure, etc. The attachment band may be enabled to use a Mobius, non-Mobius, or any twisted configuration to imply a specified functionality during a wearable device interfacing process. Additionally, a rate of twisting may be used imply a specified functionality during a wearable device interfacing process (e.g. a fast or a slow twisting motion). A tightness used with respect to interlocking the wearable devices may be additionally used to imply a specified functionality during a wearable device interfacing process. An attachment band (for a wearable device) may include individualized transparent compartments (on a front and/or back side) comprising removable transparent windows for displaying, inter alia, pictures, photographs, etc. For example, when specified pictures are aligned correctly between attachment bands, a process for facilitating specific interactions (between wearable devices) may be enabled. Attachment bands may comprise magnetic portions for attaching to users.

The following example describes an implementation process for executing wearable device actions based on a detected configuration between multiple wearable devices:

The process is initiated via a software application (on wearable device 114a or 114b) enabled to execute a secure process associated with a user digitally signing a document in the presence of a notary. The user completes a document on a tablet device as a notary observes the process. The user and notary each have a wearable device associated with their identities. The user indicates (via the wearable device) that he/she is ready to execute a notarized signature. In response, the software application prompts the user to interlink attachment bands with the notary. Upon linking with the notary, public keys are exchanged between the attachment bands to verify that the user is in the physical presence of the notary and document.

FIG. 2 illustrates an interlinking implementation scenario enabled by system 100 of FIG. 1, in accordance with embodiments of the present invention. FIG. 2 illustrates a wearable device 202a comprising a wearable device interface/computing portion 208a attached to an attachment band 204a and a wearable device 202b comprising a wearable device interface/computing portion 208b attached to an attachment band 204b. Attachment band 204a is interlinked with attachment band 204b thereby indicating a specified configuration for performing a specified action between wearable device 202a and wearable device 202b.

FIG. 3 illustrates an attachment band implementation scenario enabled by system 100 of FIG. 1, in accordance with embodiments of the present invention. FIG. 3 illustrates an attachment band 302a in an initial position, an attachment band 302b in twisted position, and s an attachment band 302c in a twisted and securely looped position. The twisted position of attachment band 302b and attachment band 302c may include any type of twisted position including any number of twists.

Figure 4:
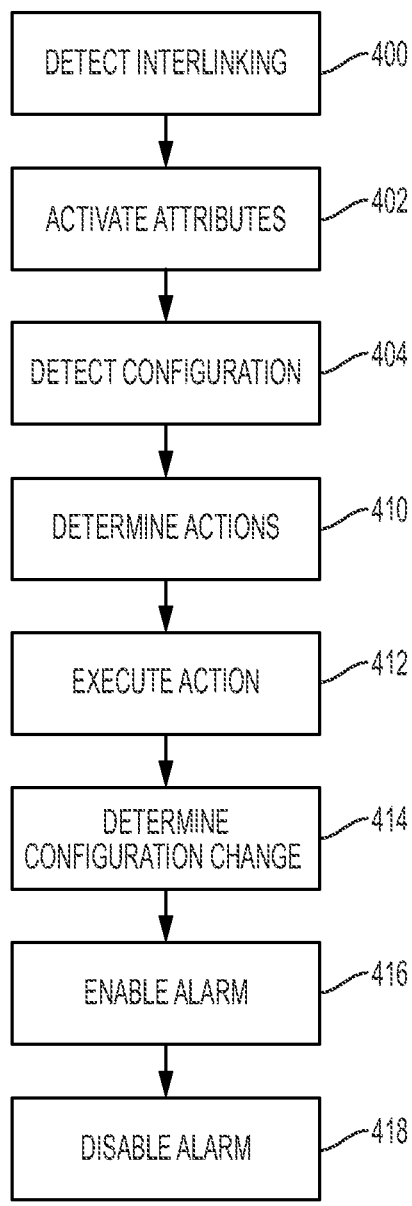
FIG. 4 illustrates an algorithm detailing a process flow enabled by the system of FIG. 1 for executing wearable device actions based on a detected configuration between multiple wearable devices, in accordance with embodiments of the present invention.

FIG. 4 illustrates an algorithm detailing a process flow enabled by system 100 of FIG. 1 for executing wearable device actions based on a detected configuration between multiple wearable devices, in accordance with embodiments of the present invention. Each of the steps in the algorithm of FIG. 4 may be enabled and executed in any order by a computer processor(s) or any type of specialized hardware executing computer code. In step 400, a body attachment band of a second wearable device of a second user is detected as being physically interlinked with a body attachment band of a first wearable device. The body attachment band of the first wearable device comprises an apparatus for attaching the first wearable device to a forearm of the first user (e.g., a watchband). The body attachment band of the second wearable device comprises an apparatus for attaching the second wearable device to a forearm of the second user. In step 402, operational attributes of the first wearable device are activated based on the detection of step 400. In step 404, a specified configuration between the body attachment band of the first wearable device and the body attachment band of the second wearable device is detected. The specified configuration may include, inter alia, a first twisted configuration of the first body attachment band of the first wearable device, a second twisted configuration of the body attachment band of the second wearable device, a gesture of the first user with respect to the first wearable device and the second wearable device, physical contact between the first wearable device and the second wearable device, an interlink interface enabled between the body portion attachment band of the first wearable device and the body portion attachment band of the second wearable device, a specified position of the first wearable device with respect to the second wearable device, etc. In step 410, specified actions associated with the operational attributes are determined. The specified actions may include, inter alia, a communication process between the first wearable device and the second wearable device, a security trust agreement between the first wearable device and the second wearable device, an integration of operations between the first wearable device and the second wearable device, etc. In step 412, a first specified action (of the specified actions) is executed (based on the specified configuration) with respect to a first operational attribute of the operational attributes. An adjusted size for each of the body portion attachment bands may be used to indicate attributes of the first specified action. Alternatively, an alignment match between visual objects on each of the body portion attachment bands may be used to indicate attributes of the first specified action. The first specified action is executed with respect to the first wearable device and the second wearable device. In step 414, it is determined that the specified configuration between the first wearable device and the second wearable device has changed. In step 416, an alarm indicating that the specified configuration between the first wearable device and the second wearable device has changed is enabled. In step 418, the alarm is disabled in response to a contact action (with respect to a body attachment band) enabled by the first user with respect to the first wearable device.

Figure 5:
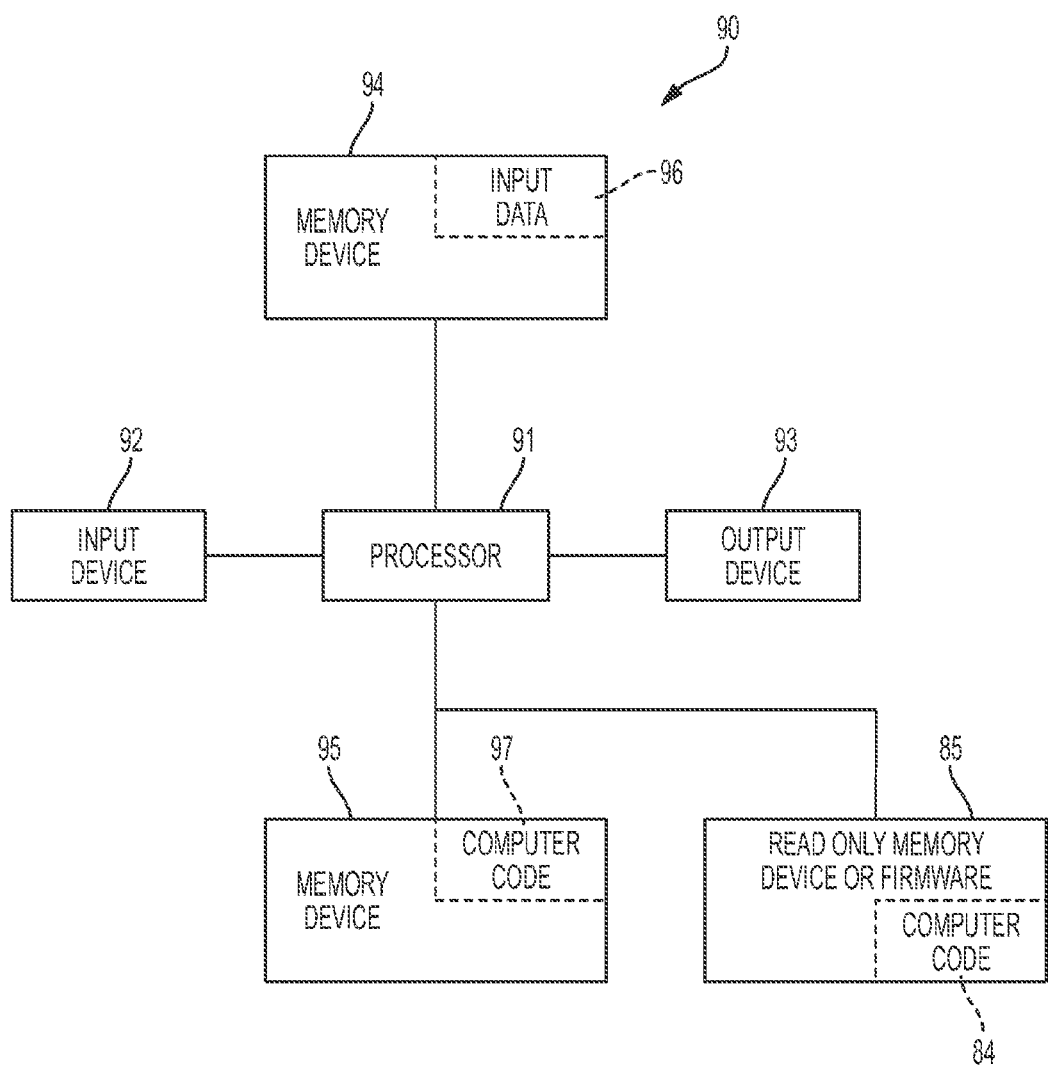
FIG. 5 illustrates a computer system used by the system of FIG. 1 for enabling a process for executing wearable device actions based on a detected configuration between multiple wearable devices, in accordance with embodiments of the present invention.

FIG. 5 illustrates a computer system 90 (e.g., control hardware 119a and 119b internal to wearable devices 114a and 114b and hardware device 14) used by or comprised by the system of FIG. 1 for enabling a process for executing wearable device actions based on a detected configuration between multiple wearable devices, in accordance with embodiments of the present invention.

Aspects of the present invention may take the form of an entirely hardware embodiment, an entirely software embodiment (including firmware, resident software, microcode, etc.) or an embodiment combining software and hardware aspects that may all generally be referred to herein as a "circuit," "module," or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing apparatus receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, device (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing device to produce a machine, such that the instructions, which execute via the processor of the computer or other programmable data processing device, create means for implementing the functions/acts specified in the flowchart and/or block diagram block or blocks. These computer readable program instructions may also be stored in a computer readable storage medium that can direct a computer, a programmable data processing device, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing device, or other device to cause a series of operational steps to be performed on the computer, other programmable device or other device to produce a computer implemented process, such that the instructions which execute on the computer, other programmable device, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The computer system 90 illustrated in FIG. 5 includes a processor 91, an input device 92 coupled to the processor 91, an output device 93 coupled to the processor 91, and memory devices 94 and 95 each coupled to the processor 91. The input device 92 may be, inter alia, a keyboard, a mouse, a camera, a touchscreen, etc. The output device 93 may be, inter alia, a printer, a plotter, a computer screen, a magnetic tape, a removable hard disk, a floppy disk, etc. The memory devices 94 and 95 may be, inter alia, a hard disk, a floppy disk, a magnetic tape, an optical storage such as a compact disc (CD) or a digital video disc (DVD), a dynamic random access memory (DRAM), a read-only memory (ROM), etc. The memory device 95 includes a computer code 97. The computer code 97 includes algorithms (e.g., the algorithm of FIG. 4) for executing wearable device actions based on a detected configuration between multiple wearable devices. The processor 91 executes the computer code 97. The memory device 94 includes input data 96. The input data 96 includes input required by the computer code 97. The output device 93 displays output from the computer code 97. Either or both memory devices 94 and 95 (or one or more additional memory devices such as read only memory device 96) may include algorithms (e.g., the algorithm of FIG. 4) and may be used as a computer usable medium (or a computer readable medium or a program storage device) having a computer readable program code embodied therein and/or having other data stored therein, wherein the computer readable program code includes the computer code 97. Generally, a computer program product (or, alternatively, an article of manufacture) of the computer system 90 may include the computer usable medium (or the program storage device).

In some embodiments, rather than being stored and accessed from a hard drive, optical disc or other writeable, rewriteable, or removable hardware memory device 95, stored computer program code 84 (e.g., including the algorithm of FIG. 4) may be stored on a static, nonremovable, read-only storage medium such as a Read-Only Memory (ROM) device 85, or may be accessed by processor 91 directly from such a static, nonremovable, read-only medium 85. Similarly, in some embodiments, stored computer program code 97 may be stored as computer-readable firmware 85, or may be accessed by processor 91 directly from such firmware 85, rather than from a more dynamic or removable hardware data-storage device 95, such as a hard drive or optical disc.

Still yet, any of the components of the present invention could be created, integrated, hosted, maintained, deployed, managed, serviced, etc. by a service supplier who offers to enable a process for executing wearable device actions based on a detected configuration between multiple wearable devices. Thus, the present invention discloses a process for deploying, creating, integrating, hosting, maintaining, and/or integrating computing infrastructure, including integrating computer-readable code into the computer system 90, wherein the code in combination with the computer system 90 is capable of performing a method for enabling a process for executing wearable device actions based on a detected configuration between multiple wearable devices. In another embodiment, the invention provides a business method that performs the process steps of the invention on a subscription, advertising, and/or fee basis. That is, a service supplier, such as a Solution Integrator, could offer to enable a process for executing wearable device actions based on a detected configuration between multiple wearable devices. In this case, the service supplier can create, maintain, support, etc. a computer infrastructure that performs the process steps of the invention for one or more customers. In return, the service supplier can receive payment from the customer(s) under a subscription and/or fee agreement and/or the service supplier can receive payment from the sale of advertising content to one or more third parties.

While FIG. 5 shows the computer system 90 as a particular configuration of hardware and software, any configuration of hardware and software, as would be known to a person of ordinary skill in the art, may be utilized for the purposes stated supra in conjunction with the particular computer system 90 of FIG. 5. For example, the memory devices 94 and 95 may be portions of a single memory device rather than separate memory devices.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A wearable device interaction method comprising:
   detecting, by a processor of a first wearable device of a first user, a body attachment band of a second wearable device of a second user physically interlinked with a body attachment band of said first wearable device, wherein said body attachment band of said first wearable device comprises an apparatus for attaching said first wearable device to a forearm of said first user, and wherein said body attachment band of said second wearable device comprises an apparatus for attaching said second wearable device to a forearm of said second user;
   detecting, by said processor, a specified configuration between said body attachment band of said first wearable device and said body attachment band of said second wearable device;
   determining, by said processor, specified actions associated with activated operational attributes of said first wearable device;
   executing, by said processor based on said specified configuration, a first specified action of said specified actions with respect to a first operational attribute of said operational attributes, said first specified action being executed with respect to said first wearable device and said second wearable device;
   determining, by said processor, that a process associated with said first specified action being executed has been modified; and
   enabling, by said processor, an alarm indicating that said process associated with said first specified action being executed has been modified.

2. The method of claim 1, wherein said specified configuration comprises a first twisted configuration of said first body attachment band of said first wearable device and a second twisted configuration of said body attachment band of said second wearable device.

3. The method of claim 1, wherein said specified configuration comprises a configuration selected from the group consisting of a gesture of said first user with respect to said first wearable device and said second wearable device and physical contact between said first wearable device and said second wearable device.

4. The method of claim 1, wherein said specified actions comprise an action selected from the group consisting of a communication process between said first wearable device and said second wearable device, a security trust agreement between said first wearable device and said second wearable device, and an integration of operations between said first wearable device and said second wearable device.

5. The method of claim 1, further comprising:
   determining, by said processor, that said specified configuration between said first wearable device and said second wearable device has changed; and
   enabling, by said processor, an alarm indicating that said specified configuration between said first wearable device and said second wearable device has changed.

6. The method of claim 5, further comprising:
   disabling, by said processor in response to a contact action enabled by said first user with respect to said first wearable device, said alarm.

7. The method of claim 1, wherein said first wearable device communicates with said second wearable device via wireless pairing communications.

8. The method of claim 1, wherein said specified configuration comprises an interlink interface enabled between said body portion attachment band of said first wearable device and said body portion attachment band of said second wearable device, and wherein an adjusted size for each of said body portion attachment bands indicates attributes of said first specified action.

9. The method of claim 1, wherein said specified configuration comprises an interlink interface enabled between said body portion attachment band of said first wearable device and said body portion attachment band of said second wearable device, and wherein an alignment match between visual objects on each of said body portion attachment bands indicates attributes of said first specified action.

10. The method of claim 1, wherein each of said first wearable device and said second wearable device comprises a sensor for monitoring positions of said first wearable device with respect to said second wearable device.

11. The method of claim 1, wherein said sensor is selected from the group consisting of an accelerometer, a humidity sensor, a pressure sensor, a proximity sensor, a temperature sensor, a heart rate monitor, an optical sensor, and a motion sensor.

12. The method of claim 1, wherein said specified configuration between said first wearable device and said second wearable device comprises a specified position of said first wearable device with respect to said second wearable device.

13. The method of claim 1, further comprising:
providing at least one support service for at least one of creating, integrating, hosting, maintaining, and deploying computer-readable code in the control hardware, said code being executed by the computer processor to implement: said detecting said body attachment band, said detecting said specified configuration, said determining, and said executing.

14. A computer program product, comprising a computer readable hardware storage device storing a computer readable program code, said computer readable program code comprising an algorithm that when executed by a processor of a first wearable device of a first user implements a wearable device interaction method, said method comprising:
detecting, by said processor, a body attachment band of a second wearable device of a second user physically interlinked with a body attachment band of said first wearable device, wherein said body attachment band of said first wearable device comprises an apparatus for attaching said first wearable device to a forearm of said first user, and wherein said body attachment band of said second wearable device comprises an apparatus for attaching said second wearable device to a forearm of said second user;
detecting, by said processor, a specified configuration between said body attachment band of said first wearable device and said body attachment band of said second wearable device;
determining, by said processor, specified actions associated with activated operational attributes of said first wearable device;
executing, by said processor based on said specified configuration, a first specified action of said specified actions with respect to a first operational attribute of said operational attributes, said first specified action being executed with respect to said first wearable device and said second wearable device;
determining, by said processor, that a process associated with said first specified action being executed has been modified; and
enabling, by said processor, an alarm indicating that said process associated with said first specified action being executed has been modified.

15. The computer program product of claim 14, wherein said specified configuration comprises a first twisted configuration of said first body attachment band of said first wearable device and a second twisted configuration of said body attachment band of said second wearable device.

16. The computer program product of claim 14, wherein said specified configuration comprises a configuration selected from the group consisting of a gesture of said first user with respect to said first wearable device and said second wearable device and physical contact between said first wearable device and said second wearable device.

17. The computer program product of claim 14, wherein said specified actions comprise an action selected from the group consisting of a communication process between said first wearable device and said second wearable device, a security trust agreement between said first wearable device and said second wearable device, and an integration of operations between said first wearable device and said second wearable device.

18. A first wearable device of a first user comprising a processor coupled to a computer-readable memory device, said computer-readable memory device comprising instructions that when executed by the processor implements a wearable device interaction method, said method comprising:
detecting, by said processor, a body attachment band of a second wearable device of a second user physically interlinked with a body attachment band of said first wearable device, wherein said body attachment band of said first wearable device comprises an apparatus for attaching said first wearable device to a forearm of said first user, and wherein said body attachment band of said second wearable device comprises an apparatus for attaching said second wearable device to a forearm of said second user;
detecting, by said processor, a specified configuration between said body attachment band of said first wearable device and said body attachment band of said second wearable device;
determining, by said processor, specified actions associated with activated operational attributes of said first wearable device;
executing, by said processor based on said specified configuration, a first specified action of said specified actions with respect to a first operational attribute of said operational attributes, said first specified action being executed with respect to said first wearable device and said second wearable device;
determining, by said processor, that a process associated with said first specified action being executed has been modified; and
enabling, by said processor, an alarm indicating that said process associated with said first specified action being executed has been modified.

19. The first wearable device of claim 18, wherein said specified configuration comprises a first twisted configuration of said first body attachment band of said first wearable device and a second twisted configuration of said body attachment band of said second wearable device.

20. The first wearable device of claim 18, wherein said specified configuration comprises a configuration selected from the group consisting of a gesture of said first user with respect to said first wearable device and said second wearable device and physical contact between said first wearable device and said second wearable device.

\* \* \* \* \*